United States Patent
Fisker et al.

(10) Patent No.: US 10,582,988 B2
(45) Date of Patent: Mar. 10, 2020

(54) AUTOMATED PRODUCTION OF DENTAL RESTORATION

(71) Applicant: 3Shape A/S, Copenhagen K (DK)

(72) Inventors: Rune Fisker, Virum (DK); Sven Nonboe, Hillerød (DK); David Fischer, Stenløse (DK)

(73) Assignee: 3SHAPE A/S, Copenhagen K (DK)

( * ) Notice: Subject to any disclaimer, the term of this patent is extended or adjusted under 35 U.S.C. 154(b) by 1166 days.

(21) Appl. No.: 14/398,280

(22) PCT Filed: May 2, 2013

(86) PCT No.: PCT/EP2013/059162
§ 371 (c)(1),
(2) Date: Oct. 31, 2014

(87) PCT Pub. No.: WO2013/164411
PCT Pub. Date: Nov. 7, 2013

(65) Prior Publication Data
US 2015/0086939 A1    Mar. 26, 2015

Related U.S. Application Data

(60) Provisional application No. 61/642,164, filed on May 3, 2012.

(30) Foreign Application Priority Data

May 3, 2012    (DK) .................................. 2012 70226

(51) Int. Cl.
*A61C 9/00*    (2006.01)
*A61C 13/00*   (2006.01)
(Continued)

(52) U.S. Cl.
CPC ................ *A61C 9/004* (2013.01); *A61C 5/77* (2017.02); *A61C 9/0053* (2013.01);
(Continued)

(58) Field of Classification Search
CPC ... A61C 9/0053; A61C 13/0006; A61C 9/004; A61C 13/0022; A61C 5/77; A61C 13/083; A61C 13/12; A61C 13/082; A61C 5/70
See application file for complete search history.

(56) References Cited

U.S. PATENT DOCUMENTS 5,690,490 A      11/1997  Cannon et al.
5,997,293 A *    12/1999  Grunenfelder ........ F27B 17/025
                                              432/206
(Continued)

FOREIGN PATENT DOCUMENTS

EP           2325771 A2     5/2011
WO       WO 2011/100978 A1  8/2011
WO       WO 2011/159520 A2  12/2011

OTHER PUBLICATIONS

International Search Report (PCT/ISA/210) dated Sep. 6, 2013, by the European Patent Office as the International Searching Authority for International Application No. PCT/EP2013/059162.

*Primary Examiner* — Charles E Anya
(74) *Attorney, Agent, or Firm* — Buchanan Ingersoll & Rooney P.C.

(57) ABSTRACT

A method for manufacturing a dental restoration for a patient, where the method includes: obtaining a 3D scan of at least a restoration site of the patient's mouth, where the manufactured dental restoration is adapted for fitting to the restoration site; obtaining a CAD design of the dental restoration; milling the restoration from a material, where the restoration is milled both on an inside surface configured for fitting to the shape of the restoration site of the patient's (Continued)

mouth and on an outside surface, where the milling is according to the obtained CAD design; transferring the milled restoration to a retention means providing a fixed known position of the restoration relative to a post-processing machinery, where the restoration is retained on the inside surface, such that the outside surface of the restoration is approachable/free/accessible; and performing post-processing of the outside surface of the restoration.

4 Claims, 8 Drawing Sheets

(51) Int. Cl.
  *A61C 5/77*    (2017.01)
  *A61C 13/08*   (2006.01)
  *A61C 13/083*  (2006.01)
  *A61C 13/12*   (2006.01)
  *A61C 5/70*    (2017.01)

(52) U.S. Cl.
  CPC ...... *A61C 13/0006* (2013.01); *A61C 13/0022* (2013.01); *A61C 13/082* (2013.01); *A61C 13/083* (2013.01); *A61C 13/12* (2013.01); *A61C 5/70* (2017.02)

(56) References Cited

U.S. PATENT DOCUMENTS

| | | | | |
|---|---|---|---|---|
| 2005/0261795 | A1* | 11/2005 | Ghosh | A61C 13/0004 700/118 |
| 2009/0136901 | A1* | 5/2009 | Cadario | A61C 13/0022 433/203.1 |
| 2009/0191506 | A1* | 7/2009 | Clark | A61C 5/062 433/41 |
| 2009/0274993 | A1* | 11/2009 | Bergstrom | A61C 13/0004 433/201.1 |
| 2011/0129790 | A1* | 6/2011 | Alphandary | A61C 19/002 433/29 |
| 2011/0171604 | A1 | 7/2011 | Durbin et al. | |
| 2011/0309540 | A1* | 12/2011 | Dittmann | F27D 5/0043 264/16 |
| 2011/0318582 | A1* | 12/2011 | Dittmann | C04B 35/6281 428/402 |
| 2013/0041629 | A1 | 2/2013 | Fisker et al. | |
| 2013/0056892 | A1 | 3/2013 | Johnson et al. | |
| 2013/0168887 | A1* | 7/2013 | Korten | A61C 13/0003 264/16 |
| 2013/0180110 | A1* | 7/2013 | Schechner | A61C 13/00 29/896.1 |
| 2013/0288026 | A1* | 10/2013 | Johnson | A61C 13/0022 428/212 |

* cited by examiner

*Fig. 3A*
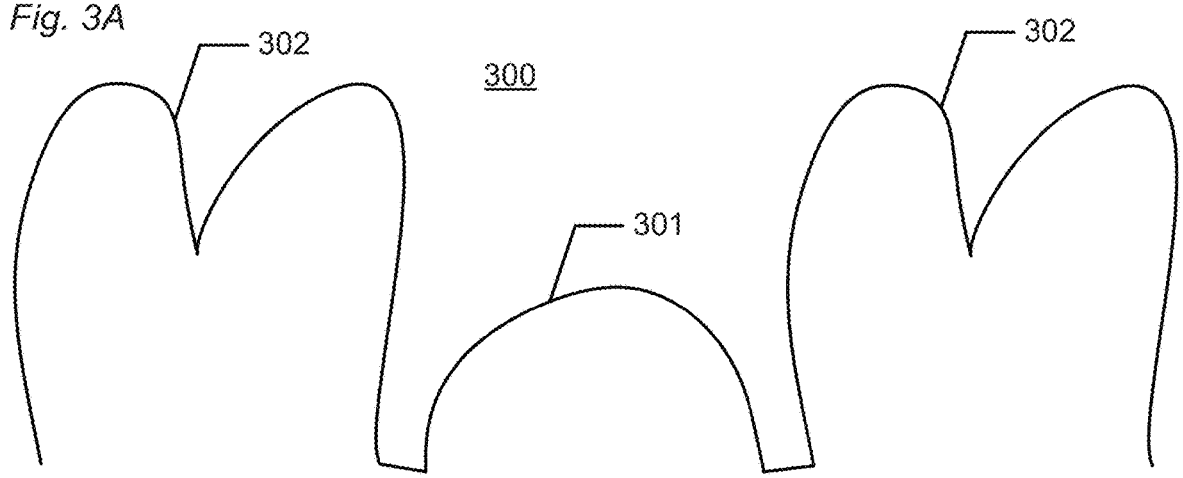
*Fig. 3B*
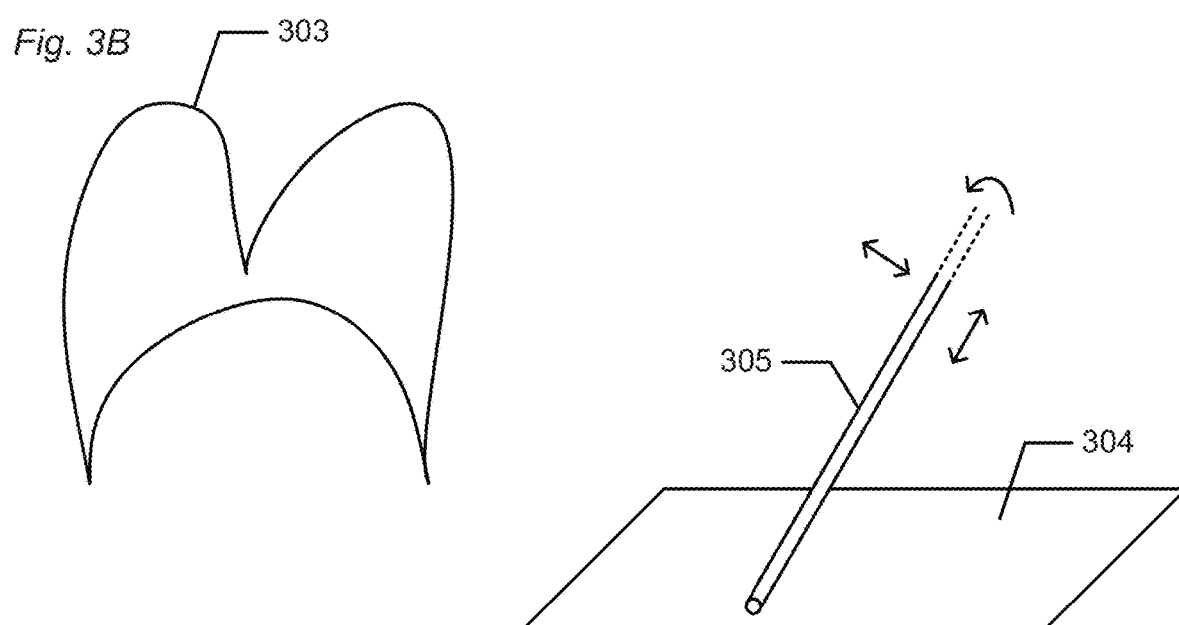
*Fig. 3C*

Transfer to retention means

Remove sprues/ connectors

AUTOMATED PRODUCTION OF DENTAL RESTORATION

FIELD OF THE INVENTION

This invention generally relates to a system and method for manufacturing/producing a dental restoration for a patient. More particularly, the invention relates to fully automated production of dental restorations.

BACKGROUND OF THE INVENTION

The Nobel Procera system from Nobel Biocare provides an at least partly automated production of dental crowns and bridges. The system provides milling gypsum blanks to form the inner shape of the restoration, and then press-fitting ceramic powders over the gypsum blanks, such that the press-fitted blanks obtains the inner shape of the restoration from the gypsum blanks.

It remains a problem to provide an improved automated production of dental restorations.

SUMMARY

Disclosed is a method for manufacturing/producing a dental restoration for a patient, where the method comprises:
  obtaining a 3D scan of at least a restoration site of the patient's mouth, where the manufactured dental restoration is adapted for fitting to the restoration site;
  obtaining a computer-aided design (CAD design) of the dental restoration;
  milling the restoration from a material, where the restoration is milled both on an inside surface for fitting to the shape of the restoration site of the patient's mouth and on an outside surface, where the milling is according to the obtained CAD design;
  transferring the milled restoration to a retention means providing a fixed known position of the restoration relative to a post-processing machinery, where the restoration is retained on the inside surface, such that the outside surface of the restoration is approachable/free/accessible; and
  performing post-processing of the outside surface of the restoration.

It is an advantage that the milled restoration is transferred to a retention means, such as a fixation die, an interface on a fixture etc., since hereby the exact position and orientation of the milled restoration is known by the processing means controlling the post-processing machinery, when the post-processing is performed, such that the post-processing can be performed correctly relative to the position of the restoration. Post-processing processes may be for example removing sprues, which are sticking out from the sides of the restoration and is a left-over from the milling procedure, and for example coloring, staining and glazing the restoration correctly, i.e. on the right areas, locations or positions on the restoration.

The post-processing machinery may be same as the milling machinery.

Furthermore, it is an advantage that the restoration is retained, held from, secured on the inside surface such that the outside surface is approachable/free/accessible/admissible for the post-processing machinery, such that post-processing can be performed on the outside surface without any retention means disturbing any part of the outside surface.

The 3D scan of the restoration site may be performed by scanning the patient's mouth directly using a handheld 3D intra oral scanner, such as 3Shape's TRIOS scanner, which is a surface scanner capturing the surface of the teeth and gums in the patient's mouth by means of scanning using light.

The 3D scan of the restoration site may alternatively be performed by scanning a physical impression of the patient's mouth using a 3D desktop scanner, such as 3Shape's desktop scanners, which are surface scanners capturing the surface of the impression of the patient's teeth and gums by scanning using light.

The 3D scan of the restoration site may alternatively be performed by scanning a physical model of the patient's mouth, where the physical model may be obtained by pouring gypsum into a physical impression of the patient's mouth. The model may also be scanned in a 3D desktop scanner, such as 3Shape's desktop scanners.

The 3D scan may be performed by means of laser light scanning, white light scanning, probe-scanning, X-ray scanning, and/or CT scanning.

The restoration site is the area in the patient's mouth where the manufactured restoration should be attached. The restoration site may be a tooth preparation, where the restoration to be attached is a crown.

In some embodiments, the inner surface of the CAD design, i.e. the part of the CAD design relating to the inner surface of the restoration, is based on the part of the obtained 3D scan relating to the restoration site. When the restoration site comprises a tooth prepared for accepting a crown, the inner surface of the CAD design be may be based on the part of the 3D scan representing the surface of the prepared tooth. This can be achieved e.g. by copying this part of the 3D scan to the CAD design. This provides that the inner surface of the milled restoration exactly matches the shape of the prepared tooth. It can also be achieved by offsetting this part of the 3D scan and generating the inner surface of the CAD design based on the offset surface. This provides that there is space for cement and glue between the prepared tooth and the inner surface of the milled restoration.

The CAD design of the restoration may be performed automatically, semi-automatically and/or by a dental technician in a CAD software program, such as 3Shape's Dental Designer software program.

According to this method the 3D scan is obtained, thus performing the 3D scan is not necessarily a part of the method. The 3D scan may be performed by a dentist or by a dental assistant in a dental clinic using an intra-oral scanner, or the 3D scan may be performed by a dental technician or by an assistant in a dental laboratory using a desktop scanner. Obtaining the 3D scan may then comprise receiving the 3D scan in the form of a digital file from the dental clinic.

According to this method the CAD design of the restoration is obtained, thus performing the CAD design is not necessarily part of the method. The CAD design may be performed by a dental technician in a dental laboratory. Obtaining the CAD design may then comprise receiving the CAD design in the form of a digital file.

The remaining steps of the method, which is milling the restoration, transferring the restoration and performing post-processing of the restoration may be performed at the same physical location, such as a milling center. Thus the 3D scanning and the CAD design will typically be performed at other physical locations than the milling center.

The restoration is milled on the inside surface to match the restoration site, e.g. the tooth preparation in the patient's mouth. The inside surface can be identical to the shape of the restoration site, and typically an offset is made for the cement space, such that there is a small gap between the restoration site and the inside surface of the restoration, where glue or cement can be applied for fixing the restoration to the restoration site.

Furthermore if the restoration is a crown for an implant, then the crown should probably be attached to an abutment of the implant, and the inside surface if the crown is then milled for fitting to the shape of the abutment.

The restoration is milled on the outside surface to provide a functional and aesthetic restoration.

The milling is performed according to the CAD design of the restoration, both for the inside surface and the outside surface.

Transferring the milled restoration may mean moving, relocating, shifting position etc. When the restoration has been milled, it should be transferred to a retention means such that post-processing of the restoration can be performed.

Transferring the milled restoration to a retention means providing a fixed known position of the restoration relative to a post-processing machinery may be performed automatically, such as by a robotic arm, or may be performed manually, such as by an operator, or may be performed as a combination of automatic and manual transferring.

It is an advantage that the retention means to which the restoration is transferred provides a fixed, known position relative to the post-processing machinery, such that the different post-processing processes can be performed on the correct, specific areas on the restoration. For example colouring of the restoration may not be uniform on the entire surface of the restoration, since some areas should for example be coloured in an A2 colour and other areas should for example be coloured in an A3 colour. Therefore the exact position of the restoration must be known by the computers, processors etc. of the post-processing machinery, such that for example the right colour can be applied on the right area on the restoration.

The position of the restoration relative to the post-processing machinery may also be detected by the post-processing mean e.g. by visual inspection of alignment marks on a plate holding the retention means.

Performing the post-processing of the outside surface of the restoration may comprise different post-processing processes, such as removing sprues or connectors from the restoration, colouring the restoration, sintering the restoration, staining and glazing the restoration, polishing the restoration, curing and baking the restoration etc. All the different post-processing processes may be performed in the post-processing machinery.

Post-processing

In some embodiments the post-processing is performed fully automated by the post-processing machinery.

It is an advantage of the method that all the post-processing processes may be fully automated, whereby no person needs to perform any manual work on the restoration.

In some embodiments the post-processing comprises removing sprues or connectors from the milled restoration.

The sprues or connectors are typically placed on the outside surface of the milled restoration, and is leftovers from the milling process. When the restoration is milled from for example a blank, then typically a number of restorations are milled from the same blank in the same process, and the sprues or connectors are the leftover material where the milled restoration is attached to the blank after milling. If the restorations are milled completely out of the blank to avoid sprues or connectors, then the restorations would fall of the blank after milling and would have to be collected in separate trays to keep track of the different restorations for different patients. So typically sprues or connectors are present on the restoration after milling, and traditionally the sprues or connectors are removed, cut off, milled away etc. manually by a person. Thus it is an advantage to have sprues or connectors removed from the milled restoration as part of the post-processing.

In some embodiments the post-processing comprises colouring the restoration based on the CAD design of the restoration.

If the material from which the restoration is milled is for example zirconium, then the restoration should be coloured. If the material is for example e.max then the restoration needs not be coloured, as the e.max material will change colour to a tooth like colour after sintering or baking.

The colouring of the milled restoration should be performed on the outside of the restoration.

The colouring may be applied by submerging the restoration in liquid colour, by spraying colour onto the restoration, and/or by painting the restoration in any suitable way.

The colouring should be based on the CAD design of the restoration, where the CAD design will also include the colour design if the restoration needs to be coloured.

In some embodiments the post-processing comprises sintering the restoration.

In some embodiments the post-processing comprises staining and glazing the restoration.

The staining and glazing is performed on the outside of the restoration to make the restoration look more natural and look like a real tooth which has been in the patient's mouth for many years. The staining may for example comprise applying dark lines on the sulcusses of the posterior teeth. The glazing may resemble the enamel of the teeth and may be applied to the restoration to obtain a natural tooth finish.

In some embodiments the post-processing comprises polishing the restoration. Typically the restoration should be polished to obtain a natural tooth finish.

In some embodiments the post-processing comprises baking and curing the restoration.

In some embodiments the post-processing comprises veneering the restoration with porcelain.

In some embodiments the post-processing comprises packing the restoration for shipping to the dentist.

All the post-processing steps or processes may be performed automatically, such as fully automatic or semi-automatic.

In some embodiments the method comprises providing an ID tag, such as a barcode, for the restoration.

The ID tag may be provided on the restoration itself, on the retention means, on the foot or plate where the retention means is located etc.

Size/Shape of Restoration During Sintering

In some embodiments the restoration is configured for maintaining its shape and size during sintering.

Some materials will maintain its shape and size during sintering while others will not, i.e. they will shrink. Materials such as for example e.max and Lava Ultimate will maintain their shape and size during sintering, whereby a restoration milled from one of these materials will also maintain its shape and size during sintering.

In some embodiments the restoration is configured for shrinking during sintering. Materials such as for example zirkonia or zirconium will not maintain its size during sintering, whereby a restoration milled from zirconium will shrink during sintering. The shape is typically maintained, whereas the size may be reduced during sintering.

In some embodiments the amount of shrinkage is predetermined, such that the exact shape and size change is known.

For zirconium the exact shape and size change is known based on the specific material mixture, and the change is about 20% for most zirconium mixtures. So the restoration should be milled to be about 25% bigger than the desired size, so that the restoration will have the right size after sintering and shrinking of 20%.

Retention Means

In some embodiments the retention means matches the inside surface of the restoration.

I.e. the top part of the retention means fits to the inside of the restoration, such that the restoration will fit exactly on the retention means at least over part of the inner surface.

In some embodiments the retention means is manufactured specifically for the restoration, such that the retention means is a custom-made retention means. This can be achieved by virtually designing the retention means based on the obtained 3D scan of the restoration site. For example, the retention means can be designed by copying the inner surface of the CAD design, such that the inner surface of the milled restoration matches a surface of the manufactured retention means. Thus the retention means is specific for the restoration.

In some embodiments the retention means is a standard retention means on which any restoration fits.

In some embodiments a first retention means is used for the restoration before sintering, and a second retention means is used for the restoration during and/or after sintering, if the restoration shrinks due to sintering.

In some embodiments the retention means is manufactured in the same material as the restoration, such that if the material shrinks during sintering the retention means is configured to shrink with the same amount as the restoration, whereby the restoration fits exactly to the retention means both before and after sintering.

In some embodiments the retention means is adapted to fit the milled restoration both before and after sintering, if the milled restoration changes its size and/or shape due to sintering.

For example if the restoration is made from zirconium, the zirconium may shrink during sintering, and ideally the retention means should fit the restoration both before sintering and after sintering, such that the restoration is properly retained, such as fixedly retained both before, during and after sintering. If the restoration becomes smaller during sintering, the retention means could also be made to become smaller by the same amount as the restoration during sintering.

Alternatively, the retention means could be too small for the restoration to begin with, such that after the restoration has shrunk due to sintering, the retention means will fit well, i.e. not be too small or too big for the restoration.

In some embodiments the retention means is made from a compressible or squeezable material, such that if the restoration shrinks during sintering, then the retention means is compressed and the restoration still fits on the retention means. An outside part of the retention means may be made of the compressible material and an inside part of the retention means may be made in a rigid material, such that the retention means is stable and steady.

The compressible material may be a kind of foam, such a polyurethane (PU).

In some embodiments the retention means is coated with a wax layer before the restoration is placed on it, and during sintering the wax layer will melt off, whereby the restoration fits on the retention means both before, and during/after sintering, if the restoration shrinks during sintering.

In some embodiments the restoration comprises a protrusion on its inside surface, and the retention means attaches to the protrusion for retaining the restoration.

Image recognition can be used to recognize the protrusion on the inside surface of the restoration.

In some embodiments transferring the restoration to the retention means comprises that the restoration is held by sprues/connectors in a first plate, such as a blank, and the first plate is then placed on a second plate comprising a retention means for the restoration such that the restoration is placed exactly on the corresponding retention means.

Interface

In some embodiments the retention means is an interface which is adapted to be attached to at least one standard fixture.

In some embodiments the retention means comprises an interface and at least one standard fixture, where the interface is adapted to be attached to the at least one standard fixture.

The interface may then be manufactured from the same material as the restoration, such that the interface for example shrinks the same amount as the restoration during sintering, whereby the restoration fits on the interface retention at all times throughout the manufacturing process.

In some embodiments the retention means is an interface which is adapted to be attached to a first standard fixture before sintering, and adapted to be attached to a second standard fixture during and/or after sintering, if the restoration shrinks during sintering.

In some embodiments the retention means comprises an interface, a first standard fixture and a second standard fixture, where the interface is adapted to be attached to the first standard fixture before sintering, and adapted to be attached to the second standard fixture during and/or after sintering, if the restoration shrinks during sintering.

In some embodiments the first retention means is a first interface which is adapted to be attached to a first standard fixture and used for the restoration before sintering, and where the second retention means is a second interface which is adapted to be attached to a second standard fixture and used for the restoration during and/or after sintering, if the restoration shrinks due to sintering.

In some embodiments a/the first retention means comprises a first interface and a first standard fixture, where the interface is adapted to be attached to the first standard fixture and used for the restoration before sintering, and where a/the second retention means comprises a second interface and a second standard fixture, where the second interface is adapted to be attached to the second standard fixture and used for the restoration during and/or after sintering, if the restoration shrinks due to sintering.

Vacuum Suction

In some embodiments the restoration is attached to the retention means by means of a vacuum suction.

Vacuum suction can be used for all the different variations of retention means, it can for example be used if a standard retention means is used, where the inside surface of the restoration does not fit exactly to the retention means, since then the restoration can be held tightly or fixedly to the retention means by means of the vacuum suction.

Vacuum suction can of course also be used when the inside of the restoration fits exactly to the retention means as an extra security for a stable fit or hold.

The vacuum suction can be applied by providing a through-hole in the retention means for the vacuum suction.

In some embodiments, the retention means is configured for allowing the restoration to be attached to the retention means by means of a vacuum suction. This may be achieved by a through-hole in the retention means which allows for the vacuum suction to hold the restoration in place at the retention means.

Colouring and Staining and Glazing

According to an aspect of the invention, a method for manufacturing/producing a dental restoration for a patient is disclosed, where the method comprises:
- obtaining a 3D scan of at least a restoration site of the patient's mouth, where the manufactured dental restoration is adapted for fitting to the restoration site;
- obtaining a computer-aided design (CAD design) of the dental restoration;
- milling the restoration from a material, where the restoration is milled both on an inside surface for fitting to the shape of the restoration site of the patient's mouth and on an outside surface, where the milling is according to the obtained CAD design;
- transferring the milled restoration to a retention means providing a fixed known position of the restoration relative to a post-processing machinery, where the restoration is retained on the inside surface, such that the outside surface of the restoration is approachable/free/accessible; and
- colouring the outside surface of the restoration.

In some embodiments the method comprises virtually/digitally designing the colouring and/or staining and/or glazing of the restoration.

The virtual/digital design of the colouring, staining and/or glazing can be performed for simulating the visual appearance of the final restoration.

In some embodiments the virtual/digital design of the colouring of the restoration comprises using a virtual/digital paint tool for simulating applying colour on the restoration.

The virtual/digital paint tool may be a virtual paint-brush, sprayer, or reservoir filled with colour etc. Applying the colour may be simulated by simulating spraying, painting, submerging into reservoir etc.

In some embodiments the virtual/digital design of the colouring of the restoration is at least partly based on a colour measurement of the patient's existing teeth.

The colouring may comprise using different colour codes, such as A2, A3, A4 etc.

Photo Realistic Rendering

In some embodiments the method comprises performing photo realistic rendering of coloring and/or staining and/or glazing of the restoration.

In some embodiments the method comprises performing colouring and/or staining and/or glazing of the milled restoration.

Colouring of the restoration may for example be performed when zirconium is used as the material, since zirconium does not have a natural tooth colour. Colouring is not necessarily used when for example e.max is the used material, since the e.max will obtain a natural tooth colour after sintering and/or after curing/baking.

For zirconium, the restoration, such as a coping, may for example be submerged into a coloured liquid or paint just one time. The zirconium may be porous or with small holes or perforations in the material, so the colour may penetrate the restoration to inner layers such that it corresponds to adding more colour layers on the restoration. For a restoration, such as a full crown, the crown may for example be submerged fully or partly into different coloured liquids or paints a number of times for providing natural color layers on all areas of the crown.

In some embodiments the colouring and/or staining is performed by means of spraying colour paint and/or stain onto the restoration.

In some embodiments the colouring and/or staining is performed by means of submerging the restoration into one or more reservoirs comprising liquid colour paint.

In some embodiments the glazing is performed by means of spraying the restoration with the glaze and/or by means of submerging the restoration into a reservoir comprising glaze.

If more restorations should have the same colouring and/or staining and/or glazing, then all these restorations may be coloured and/or stained and/or glazed at the same time by submerging them all at the same time into the reservoir(s) or by spraying them all at the same time. If the restorations which should have the same colouring are milled from the same blank, the blank itself can be coloured instead of colouring the restorations after milling.

The staining may alternatively be added manually by hand if this is more effective, cheaper, less time consuming, or provides a better and more natural-looking result etc.

In some embodiments the colouring and/or staining and/or glazing is performed in the post-processing machinery, which is furthermore adapted for comprising one or more of:
- means for cutting sprues or connectors of the restoration;
- means for sintering;
- means for polishing;
- means for curing/baking.

In some embodiments the post-processing machinery comprises a number of different tools adapted for performing the different post-processing processes.

Thus it is an advantage that the machinery is adapted for alternating between the different tools, when the different processes are to be performed. A robotic arm may be used for alternating between the different processes of the machinery.

Milling

In some embodiments the material which the restoration is milled from is held in a milling machine, such that both sides of the material is configured for being milled, whereby both the inside surface and the outside surface of the restoration is adapted to be milled.

In some embodiments, the material which the restoration is milled from is held in a milling machine in such a way that both sides of the material are accessible to the milling tool of the milling machine. Thereby both the inside surface and the outside surface of the restoration can be milled without changing the way the milling material is held by the milling machine.

Restoration

In some embodiments the restoration is a crown, a bridge, an inlay, an onlay, a coping, a veneer, an implant, and/or an implant abutment.

Restoration Site

In some embodiments the restoration site is a preparation, a die, a hole in the jaw for an implant and/or an implant abutment.

Material

In some embodiments the material which the restoration is milled from is a blank. Zirconium is an example of a material which is provided as a blank.

In some embodiments the material which the restoration is milled from is a block. e.max is an example of a material which is provided from a block.

The e-max material can for example be IPS e.max Press, IPS e.max ZirPress, IPS e.max CAD, IPS e.max ZirCAD etc.

The material can in general be e.max, Lava Ultimate restorative, feldspatic glass ceramic, lithium disilicate, zirconium also known as zirconium oxide, zirkonia or Prettau Zirkonia.

In some embodiments the method is a computer-implemented method or at least a partly computer-implemented method.

Scanning

Obtaining a three dimensional representation of the surface of an object by scanning the object in a 3D scanner can be denoted 3D modeling, which is the process of developing a mathematical representation of the three-dimensional surface of the object via specialized software. The product is called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view.

The "picture" produced by a 3D scanner describes the distance to a surface at each point in the picture.

For most situations, a single a scan or sub-scan will not produce a complete model of the object. Multiple sub-scans, such as 5, 10, 12, 15, 20, 30, 40, 50, 60, 70, 80, 90 or in some cases even hundreds, from many different directions may be required to obtain information about all sides of the object. These sub-scans are brought in a common reference system, a process that may be called alignment or registration, and then merged to create a complete model.

A triangulation 3D laser scanner uses laser light to probe the environment or object. A triangulation laser shines a laser on the object and exploits a camera to look for the location of the laser dot. Depending on how far away the laser strikes a surface, the laser dot appears at different places in the camera's field of view. This technique is called triangulation because the laser dot, the camera and the laser emitter form a triangle. A laser stripe, instead of a single laser dot, may be used and is then swept across the object to speed up the acquisition process.

Structured-light 3D scanners project a pattern of light on the object and look at the deformation of the pattern on the object. The pattern may be one dimensional or two dimensional. An example of a one dimensional pattern is a line. The line is projected onto the object using e.g. an LCD projector or a sweeping laser. A camera, offset slightly from the pattern projector, looks at the shape of the line and uses a technique similar to triangulation to calculate the distance of every point on the line. In the case of a single-line pattern, the line is swept across the field of view to gather distance information one strip at a time.

An example of a two-dimensional pattern is a grid or a line stripe pattern. A camera is used to look at the deformation of the pattern, and an algorithm is used to calculate the distance at each point in the pattern. Algorithms for multistripe laser triangulation may be used.

Iterative Closest Point (ICP) is an algorithm employed to minimize the difference between two clouds of points. ICP can be used to reconstruct 2D or 3D surfaces from different scans or sub-scans. The algorithm is conceptually simple and is commonly used in real-time. It iteratively revises the transformation, i.e. translation and rotation, needed to minimize the distance between the points of two raw scans or sub-scans. The inputs are: points from two raw scans or sub-scans, initial estimation of the transformation, criteria for stopping the iteration. The output is: refined transformation. Essentially the algorithm steps are:

1. Associate points by the nearest neighbor criteria.
2. Estimate transformation parameters using a mean square cost function.
3. Transform the points using the estimated parameters.
4. Iterate, i.e. re-associate the points and so on.

The present invention relates to different aspects including the method described above and in the following, and corresponding methods, devices, apparatuses, systems, uses, kits and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for manufacturing/producing a dental restoration for a patient, where the system comprises:

means for obtaining a 3D scan of at least a restoration site of the patient's mouth, where the manufactured dental restoration is adapted for fitting to the restoration site;

means for obtaining a computer-aided design (CAD design) of the dental restoration;

means for milling the restoration from a material, where the restoration is milled both on an inside surface for fitting to the shape of the restoration site of the patient's mouth and on an outside surface, where the milling is according to the obtained CAD design;

means for transferring the milled restoration to a retention means providing a fixed known position of the restoration relative to a post-processing machinery, where the restoration is retained on the inside surface, such that the outside surface of the restoration is approachable/free/accessible; and means for performing post-processing of the outside surface of the restoration.

Means for obtaining a 3D scan may be a software feature in the processing unit of the system providing that the 3D scan can be loaded into a computer of the system. The 3D scan may be performed at a different physical location and the 3D scan can then be send, e.g. electronically, to the computer of the system, such that the 3D scan can be used in the system.

Means for obtaining a CAD design may be a software feature in the processing unit of the system providing that the CAD design can be loaded into a computer of the system. The CAD design may be performed at a different physical location and the CAD design can then be send, e.g. electronically, to the computer of the system, such that the CAD design can be used in the system.

Means for milling may be a milling machine, a drill, a grinder, a cutting and shaping equipment etc.

Means for transferring may be a robotic arm, a conveyor band, a machine configured for transferring etc.

Means for performing post-processing may be colouring equipment such as spray nozzles, reservoirs comprising paint etc.; sintering equipment such as a sinter oven; staining equipment such as a paint brush or spray nozzle; baking and curing equipment such as an baking oven etc.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 3A-3F show schematic examples of some of the different steps of the method.

DETAILED DESCRIPTION

In the following description, reference is made to the accompanying figures, which show by way of illustration how the invention may be practiced.

Figure 1:
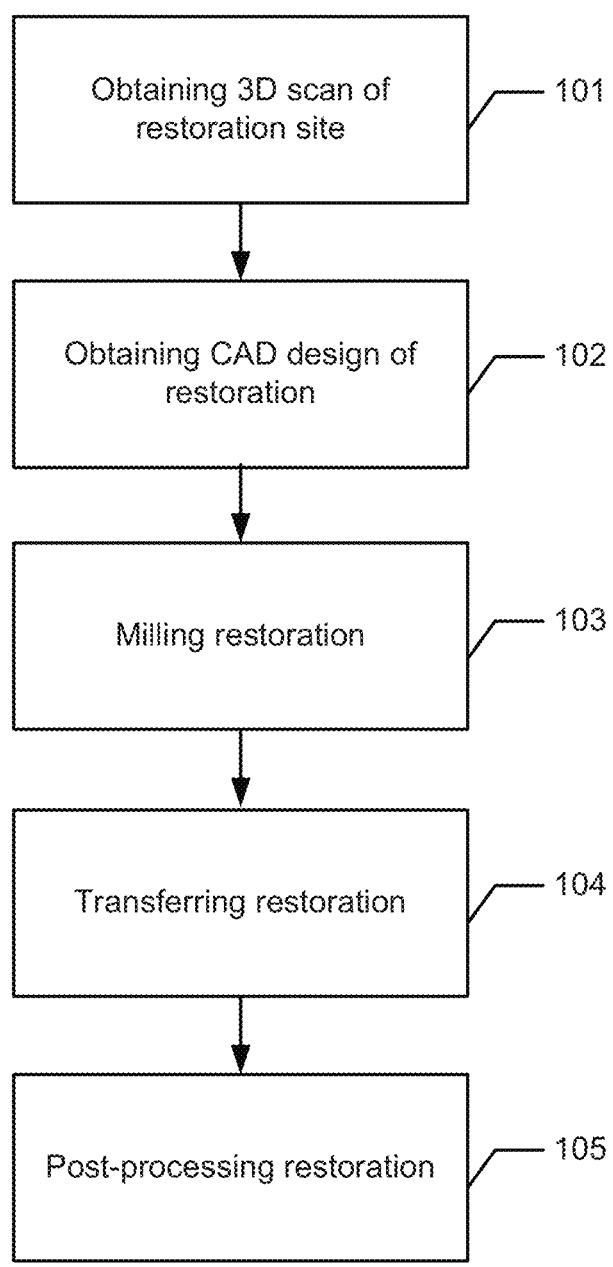
FIG. 1 shows an example of a method for manufacturing/producing a dental restoration for a patient.

FIG. 1 shows an example of a method for manufacturing/producing a dental restoration for a patient.

In step 101 a 3D scan of at least a restoration site of the patient's mouth, where the manufactured dental restoration is adapted for fitting to the restoration site is obtained.

In step 102 a computer-aided design (CAD design) of the dental restoration is obtained.

In step 103 the restoration is milled from a material, where the restoration is milled both on the inside surface configured for fitting to the shape of the restoration site of the patient's mouth and on the outside surface, where the milling is according to the obtained CAD design.

In step 104 the milled restoration is transferred to a retention means providing a fixed known position of the restoration relative to a post-processing machinery, where the restoration is retained on the inside surface, such that the outside surface of the restoration is approachable/free/accessible.

In step 105 post-processing of the outside surface of the restoration is performed.

Figure 2:
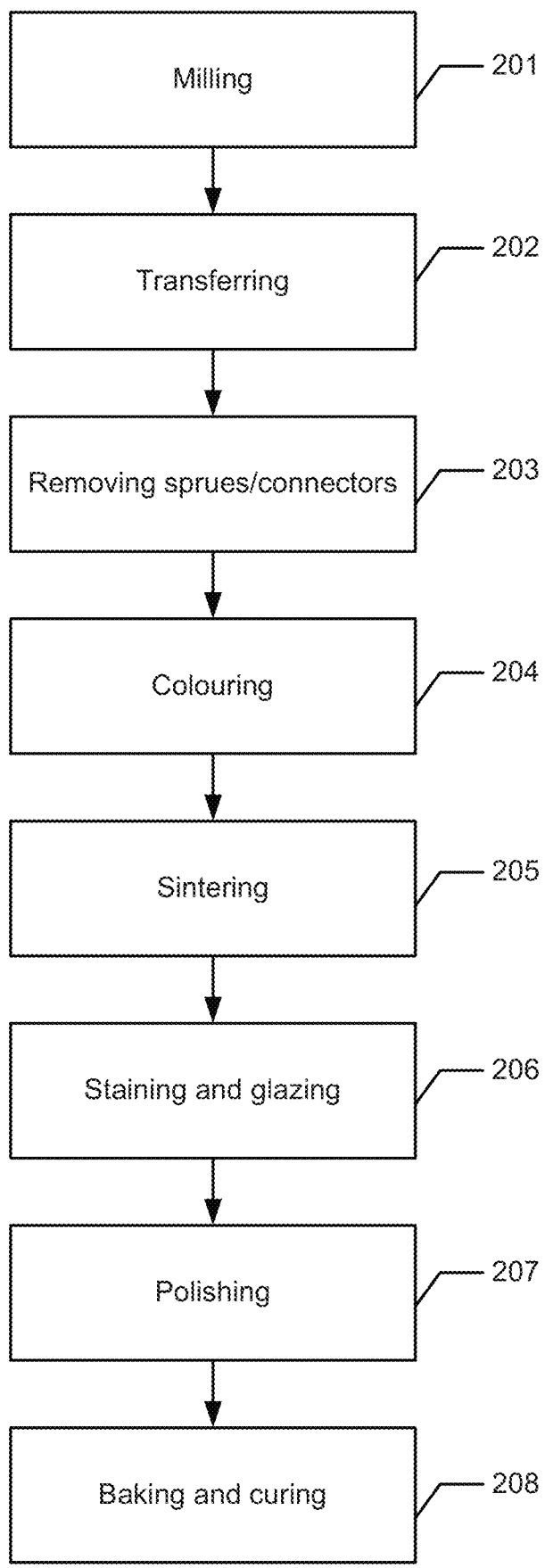
FIG. 2 shows an example of a process or method for manufacturing/producing a dental restoration for a patient, where the process can be fully automated.

FIG. 2 shows an example of a process or method for manufacturing/producing a dental restoration for a patient, where the process can be fully automated.

Prior to or as part of performing the process or method, a 3D scan of the restoration site may be obtained, and a CAD design of the restoration may be obtained, see FIG. 1.

In step 201 the restoration is milled from a material, where the restoration is milled both on the inside surface configured for fitting to the shape of the restoration site of the patient's mouth and on the outside surface, where the milling is according to the obtained CAD design.

In step 202 the milled restoration is transferred to a retention means providing a fixed known position of the restoration relative to a post-processing machinery, where the restoration is retained on the inside surface, such that the outside surface of the restoration is approachable/free/accessible.

The next steps may all be performed as part of the post-processing of the restoration, but not all steps may be required for a specific material or case.

In step 203 sprues or connectors may be removed from the restoration.

In step 204 the restoration may be coloured.

In step 205 the restoration may be sintered.

In step 206 the restoration may be stained and glazed.

In step 207 the restoration may be polished.

In step 208 the restoration may be cured and baked.

FIGS. 3A-F show schematic examples of some of the different steps of the method.

FIG. 3A shows an example of an obtained 3D scan 300 of at least a restoration site 301 of the patient's mouth, where the manufactured dental restoration is adapted for fitting to the restoration site. Two neighbor teeth 302 are also seen. The 3D scan is shown as a 2D drawing, but it is understood that the real 3D scan will be in 3D and can be turned and seen from all sides on a computer screen.

FIG. 3B shows an example of a computer-aided design (CAD) design of the restoration 303. The CAD design is shown as a 2D drawing, but it is understood that the real CAD drawing will be in 3D and can be turned and seen from all sides on a computer screen.

FIG. 3C shows an example of milling the restoration 303 from a material 304. Milling is performed by a milling tool 305. The material may for example be an e.max block.

Figure 3D:
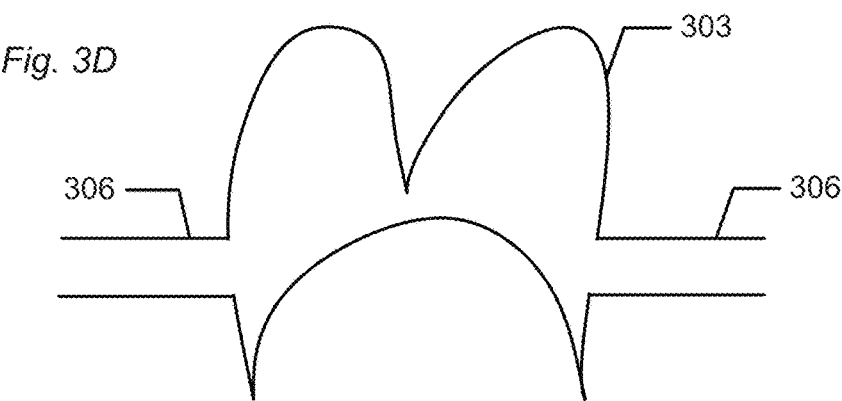

FIG. 3D shows an example of the milled restoration 303 which is about to be transferred to a retention means. The milled restoration has sprues 306 or connectors 306 on its sides as a leftover from the milling.

Figure 3E:
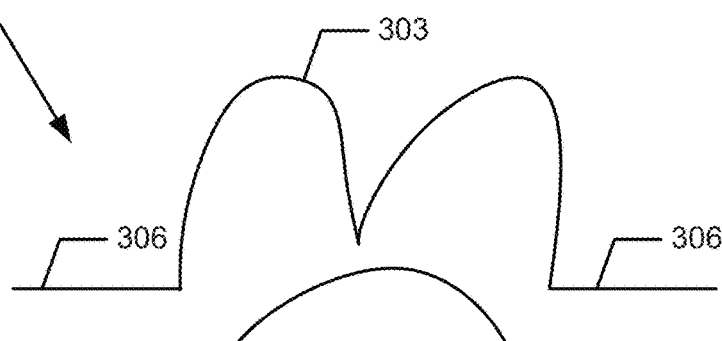

FIG. 3E shows an example where the milled restoration 303 has been transferred to the retention means 307. The sprues 306 or connectors 306 are about to be removed from the restoration 303.

Figure 3F:
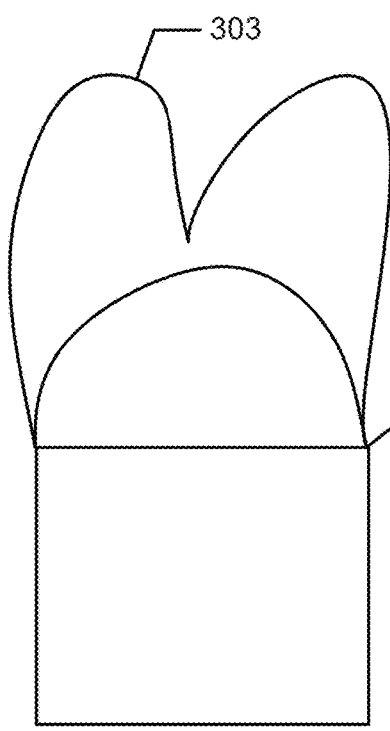

FIG. 3F shows an example where the sprues or connectors have been cut off the restoration 303.

FIGS. 4A-D show examples of the retention means before and after sintering the restoration.

Figure 4A:
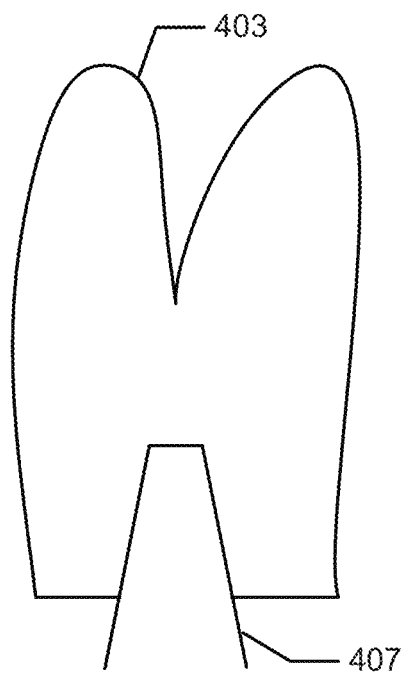
FIGS. 4A-4D show examples of the retention means before and after sintering the restoration.

FIG. 4A shows an example of the restoration 403 before sintering. The restoration is arranged on a retention means 407.

Figure 4B:
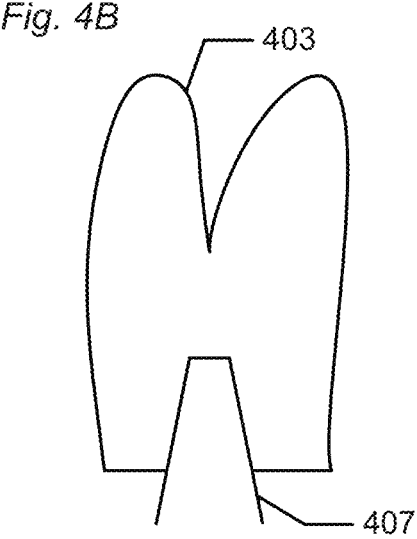

FIG. 4B shows an example of the restoration 403 after sintering. Both the restoration 403 and the retention means 407 have decreased in size during sintering. The extent to which the restoration 403 and the retention means 407 have decreased is the same, such that the restoration 403 still fits exactly to the retention means 407 after sintering. If the material of the restoration and the retention means is the same, then the amount that they both shrink during sintering will be the same.

Figure 4C:
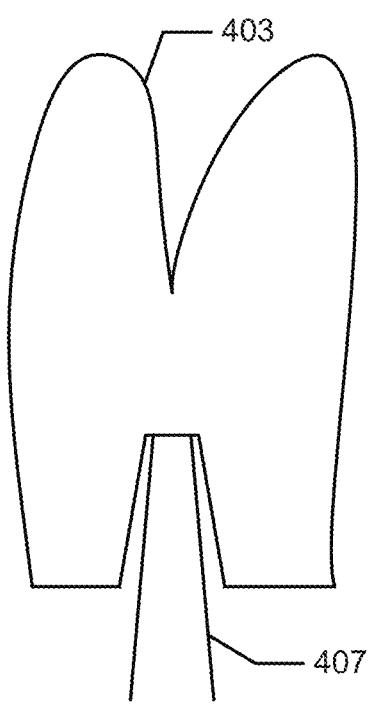

FIG. 4C shows an example where the restoration 403 is shifted or moved or transferred to a smaller retention means 407 before sintering. This can be done if the retention means 407 is not made from the same material as the restoration, and the restoration is made from a material which will shrink during sintering.

Figure 4D:
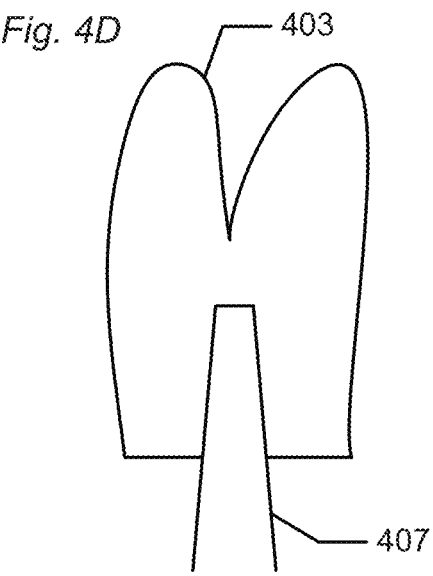

FIG. 4D shows an example where the restoration 403 has been sintered and shrunk, but where the retention means 407 has not changed size, so the small retention means from FIG. 4C now fits exactly to the restoration, as the restoration has become smaller after sintering.

During sintering the restorations may be arranged in any way. The restorations may be arranged straight, e.g. resting on their retention means, they may be arranged upside-down, not resting on their retention means, they may lay on one side or the other, be held by a tray etc.

Figure 5A:
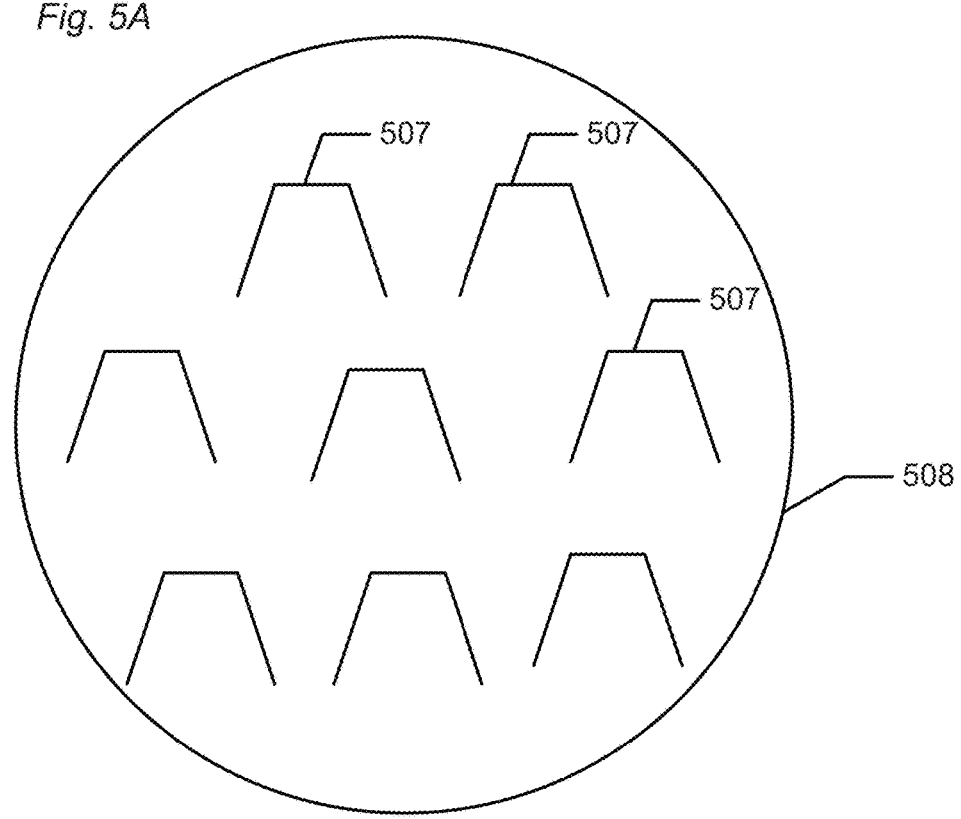
FIGS. 5A and 5B show examples of transferring restorations to retention means.
Figure 5B:
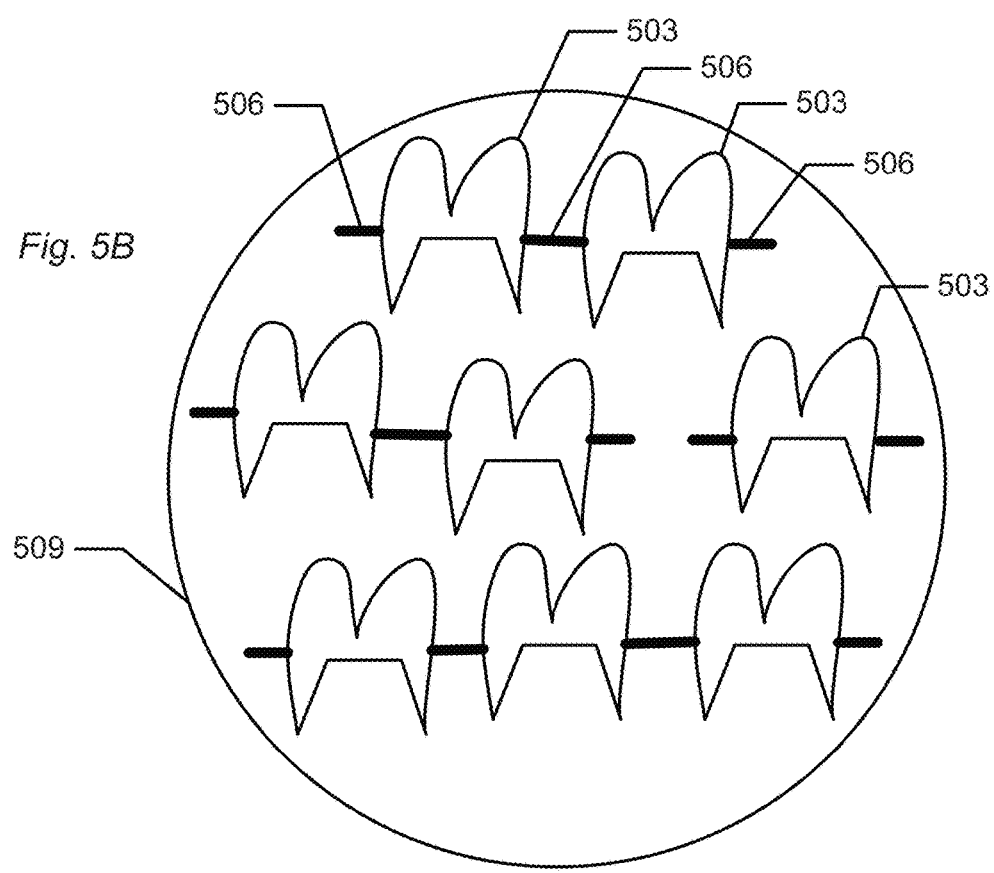

FIGS. 5A-B show an example of transferring restorations to retention means.

FIG. 5A shows an example of a plate 508 comprising a number of retention means 507.

FIG. 5B shows an example of a plate 509 comprising a number of milled restorations 503. The milled restorations 503 are still connected to the plate 509 by means of sprues 506.

Each restoration 503 can be transferred to its corresponding retention means 507 by placing the plate 509 comprising the restorations over the plate 508 comprising the retention means 507 and lowering the plate 509 until each restoration rests on its corresponding retention means. Then the sprues 506 can be cut off, and the empty plate 509 can now be removed, and each restoration will be retained on its corresponding retention means.

Figure 6A:
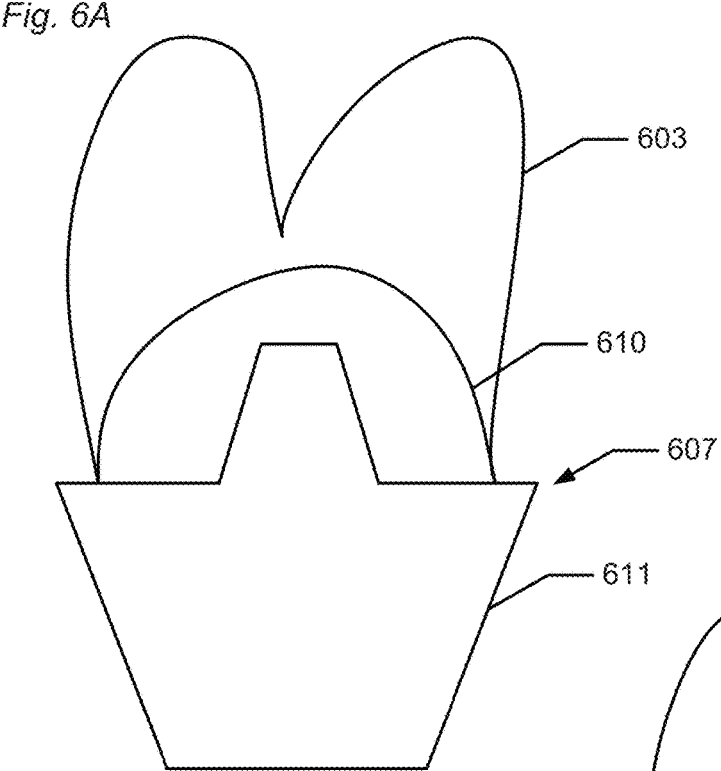
FIGS. 6A-6C show different examples of retention means.
Figure 6B:
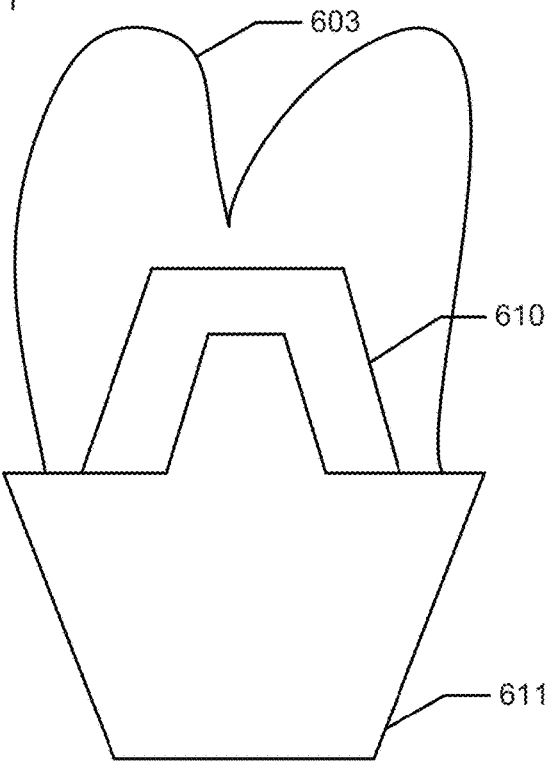
Figure 6C:
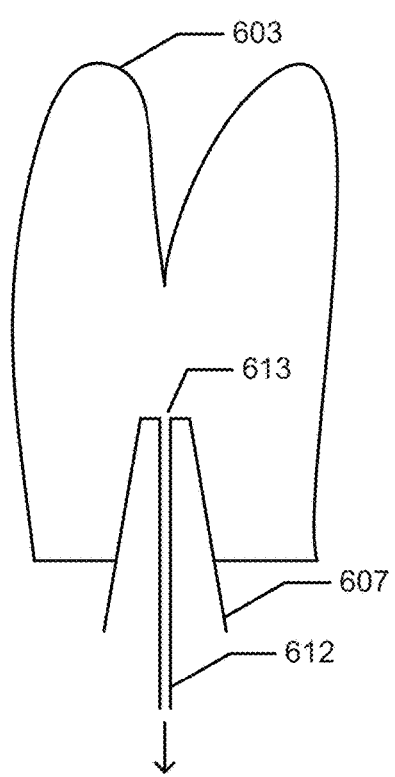

FIGS. 6A-C show different examples of retention means.

In FIGS. 3A-F, 4A-D, and 5A-B different examples of retention means are shown. FIGS. 6A-C show further examples of retention means.

FIG. 6A shows an example of a retention means 607 comprising an interface 610 and a fixture 611, or where the retention means 607 is the interface 610.

A restoration 603 is arranged on the retention means. The interface 610 has a rounded off shape at the surface pointing against the inside of the restoration 603. The interface 610 may be made from the same material as the restoration 603 such that the interface and the restoration shrink by the same amount during sintering, if the material is subject to shrinking, whereby the restoration fits on the interface both before and during/after sintering.

FIG. 6B shows an example of a retention means 607 comprising an interface 610 and a fixture 611, or where the retention means 607 is the interface 610.

A restoration 603 is arranged on the retention means. The interface 610 has a straight shape at the surface pointing against the inside of the restoration 603. The interface 610 may be made from the same material as the restoration 603 such that the interface and the restoration shrink by the same amount during sintering, if the material is subject to shrinking, whereby the restoration fits on the interface both before and during/after sintering.

FIG. 6C shows an example of a retention means 607 which is configured for allowing the restoration 603 to be attached to the retention means by means of a vacuum suction 612. The retention means 607 comprises a through-hole 613 through which the vacuum suction 612 can be applied. The vacuum suction ensures that the restoration 603 is fixedly attached to the retention means 607, which can for example be used if the inside surface of the restoration 603 does not exactly match the shape of the retention means, e.g. if a standard retention means is used.

Figure 7A:
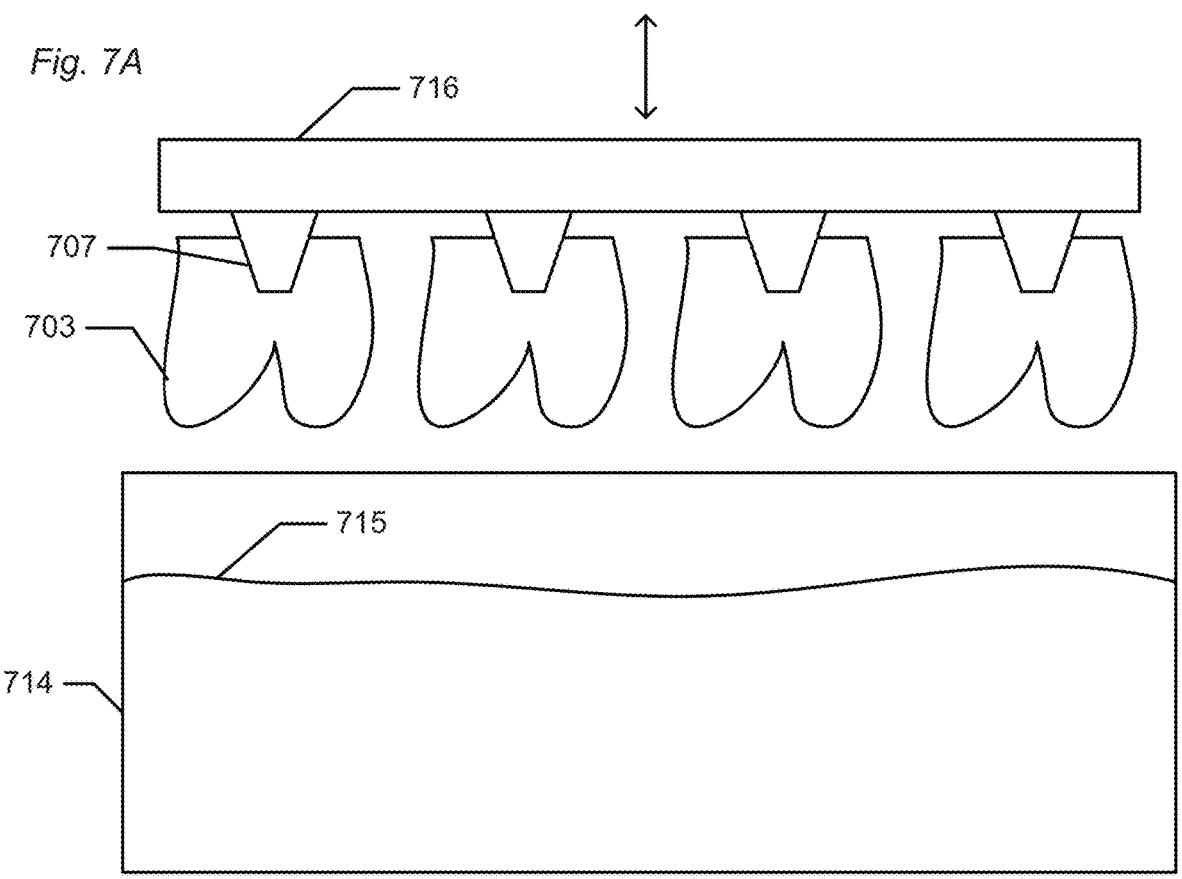
FIGS. 7A and 7B show examples of colouring the restorations.
Figure 7B:
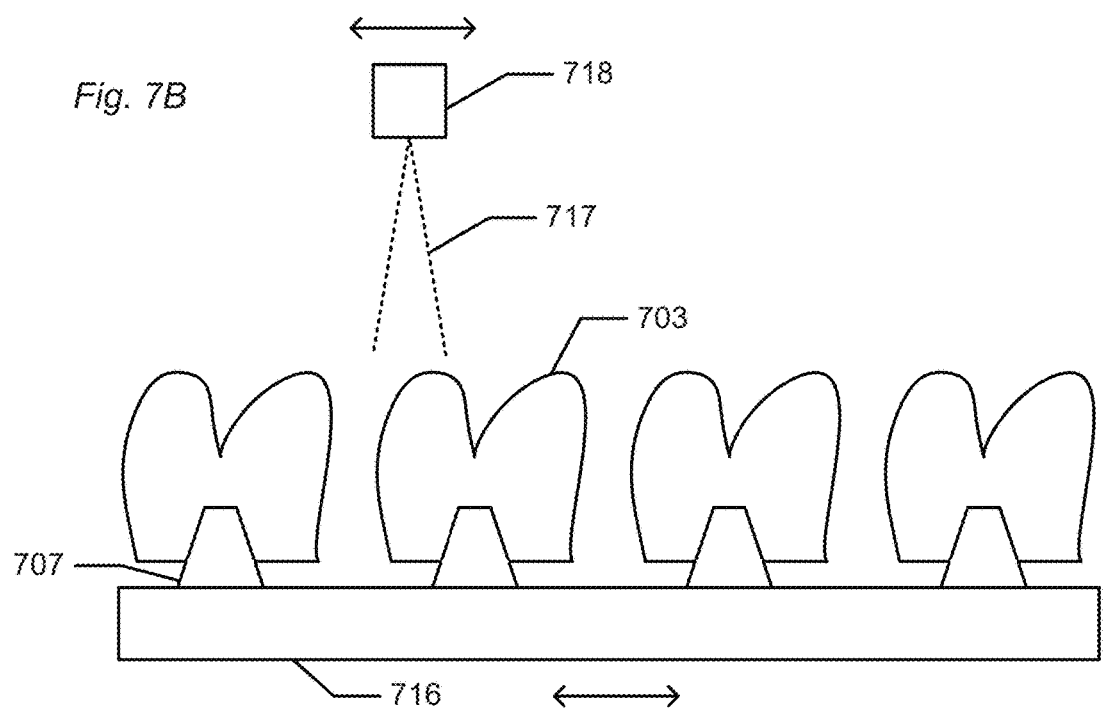

FIGS. 7A-B show examples of colouring the restorations.

In FIG. 7A the restorations 703 are coloured in a reservoir 714 containing paint 715. The restorations 703 are attached on their retention means 707, and the retention means 707 are fixed on a bar 716. The bar 716 with the restorations 703 can be submerged into the reservoir whereby the restorations are coloured. The restorations may be submerged into different colour reservoirs to obtain a suitable colouring of the restoration.

In FIG. 7B the restorations 703 are coloured by spraying paint 717 on them by means of one or more spray nozzle(s) 718. One or more restorations 703 may be coloured at the same time, depending on the reach/range/extent of the spray nozzle. The restorations 703 are arranged on their retention means 707, and the retention means 707 are arranged on a bar 716. The bar 716 and/or the spray nozzle 718 can move sideways such that all restorations on the bar can be painted.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

The invention claimed is:

1. A method for manufacturing/producing a dental restoration for a patient, where the method comprises:
   obtaining a 3D scan of at least a restoration site of the patient's mouth, where the manufactured dental restoration is adapted for fitting to the restoration site;
   obtaining a computer-aided design (CAD design) of the dental restoration;
   milling the restoration from a material, where the restoration is milled both on an inside surface configured for fitting to the shape of the restoration site of the patient's mouth and on an outside surface, where the milling is according to the obtained CAD design;
   transferring the milled restoration to a retention means providing a fixed known position of the restoration relative to a post-processing machinery, where the restoration is retained on the inside surface, such that the outside surface of the restoration is approachable/free/accessible; and
   performing post-processing of the outside surface of the restoration, wherein the post-processing comprises sintering the restoration,
   wherein the retention means is an interface which is adapted to be attached to a first standard fixture before sintering, and adapted to be attached to a second standard fixture during and/or after sintering, if the restoration shrinks during sintering.

2. A method for manufacturing/producing a dental restoration for a patient, where the method comprises:

obtaining a 3D scan of at least a restoration site of the patient's mouth, where the manufactured dental restoration is adapted for fitting to the restoration site;

obtaining a computer-aided design (CAD design) of the dental restoration;

milling the restoration from a material, where the restoration is milled both on an inside surface configured for fitting to the shape of the restoration site of the patient's mouth and on an outside surface, where the milling is according to the obtained CAD design;

transferring the milled restoration to a retention means providing a fixed known position of the restoration relative to a post-processing machinery, where the restoration is retained on the inside surface, such that the outside surface of the restoration is approachable/free/accessible; and performing post-processing of the outside surface of the restoration, wherein the post-processing comprises sintering the restoration, wherein the retention means comprises an interface, a first standard fixture and a second standard fixture, where the interface is adapted to be attached to the first standard fixture before sintering, and adapted to be attached to the second standard fixture during and/or after sintering, if the restoration shrinks during sintering.

3. A method for manufacturing/producing a dental restoration for a patient, where the method comprises:

obtaining a 3D scan of at least a restoration site of the patient's mouth, where the manufactured dental restoration is adapted for fitting to the restoration site;

obtaining a computer-aided design (CAD design) of the dental restoration;

milling the restoration from a material, where the restoration is milled both on an inside surface configured for fitting to the shape of the restoration site of the patient's mouth and on an outside surface, where the milling is according to the obtained CAD design;

transferring the milled restoration to a retention means providing a fixed known position of the restoration relative to a post-processing machinery, where the restoration is retained on the inside surface, such that the outside surface of the restoration is approachable/free/accessible; and performing post-processing of the outside surface of the restoration, wherein the post-processing comprises sintering the restoration, wherein a first retention means is used for the restoration before sintering, and a second retention means is used for the restoration during and/or after sintering, if the restoration shrinks due to sintering, wherein the first retention means is a first interface which is adapted to be attached to a first standard fixture and used for the restoration before sintering, and where the second retention means is a second interface which is adapted to be attached to a second standard fixture and used for the restoration during and/or after sintering, if the restoration shrinks due to sintering.

4. A method for manufacturing/producing a dental restoration for a patient, where the method comprises:

obtaining a 3D scan of at least a restoration site of the patient's mouth, where the manufactured dental restoration is adapted for fitting to the restoration site;

obtaining a computer-aided design (CAD design) of the dental restoration;

milling the restoration from a material, where the restoration is milled both on an inside surface configured for fitting to the shape of the restoration site of the patient's mouth and on an outside surface, where the milling is according to the obtained CAD design;

transferring the milled restoration to a retention means providing a fixed known position of the restoration relative to a post-processing machinery, where the restoration is retained on the inside surface, such that the outside surface of the restoration is approachable/free/accessible; and performing post-processing of the outside surface of the restoration, wherein the post-processing comprises sintering the restoration, wherein a first retention means is used for the restoration before sintering, and a second retention means is used for the restoration during and/or after sintering, if the restoration shrinks due to sintering, wherein the first retention means comprises a first interface and a first standard fixture, where the interface is adapted to be attached to the first standard fixture and used for the restoration before sintering, and where the second retention means comprises a second interface and a second standard fixture, where the second interface is adapted to be attached to the second standard fixture and used for the restoration during and/or after sintering, if the restoration shrinks due to sintering.

* * * * *